United States Patent
Cheng et al.

(10) Patent No.: US 10,918,263 B2
(45) Date of Patent: *Feb. 16, 2021

(54) ADJUSTABLE ENDOSCOPE SHEATH

(71) Applicant: Gyrus ACMI, Inc., Southborough, MA (US)

(72) Inventors: Ming J. Cheng, W. Warwick, RI (US); John P. Flynn, Collierville, TN (US)

(73) Assignee: Gyrus Acmi, Inc., Southborough, MA (US)

( * ) Notice: Subject to any disclaimer, the term of this patent is extended or adjusted under 35 U.S.C. 154(b) by 395 days.

This patent is subject to a terminal disclaimer.

(21) Appl. No.: 15/410,016

(22) Filed: Jan. 19, 2017

(65) Prior Publication Data

US 2017/0127917 A1 May 11, 2017

Related U.S. Application Data

(63) Continuation of application No. 14/551,440, filed on Nov. 24, 2014, now Pat. No. 9,585,547.

(51) Int. Cl.
| | |
|---|---|
| *A61B 1/12* | (2006.01) |
| *A61B 1/015* | (2006.01) |
| *A61B 1/06* | (2006.01) |
| *A61B 1/00* | (2006.01) |

(52) U.S. Cl.
CPC ........ *A61B 1/00135* (2013.01); *A61B 1/0014* (2013.01); *A61B 1/00128* (2013.01); *A61B 1/015* (2013.01); *A61B 1/0661* (2013.01); *A61B 1/126* (2013.01)

(58) Field of Classification Search
USPC ......... 600/121–125, 136–137, 155–158, 173
See application file for complete search history.

(56) References Cited

U.S. PATENT DOCUMENTS

| | | | |
|---|---|---|---|
| 4,254,762 A | 3/1981 | Yoon | |
| 4,281,646 A | 8/1981 | Kinoshita | |
| 4,312,375 A | 1/1982 | Leinemann | |
| 4,548,197 A | 10/1985 | Kinoshita | |

(Continued)

FOREIGN PATENT DOCUMENTS

| | | |
|---|---|---|
| EP | 0374727 A1 | 6/1990 |
| JP | H05/038323 A | 2/1993 |

(Continued)

OTHER PUBLICATIONS

US 5,772,579 A, 06/1998, Reisdorf (withdrawn)
(Continued)

*Primary Examiner* — Matthew J Kasztejna
(74) *Attorney, Agent, or Firm* — Schwegman Lundberg & Woessner, P.A.

(57) ABSTRACT

An endoscope sheath is provided comprising a sheath tube extending along a longitudinal axis between a proximal end and a distal end, the sheath tube is configured to receive at least a portion of an endoscope; a hub connected to the proximal end of the sheath tube; and a hub adapter engaging the hub and configured to engage the endoscope, wherein the sheath tube can rotate about the longitudinal axis without rotation of the hub adapter, and wherein the sheath tube is restricted from moving axially along the longitudinal axis relative to the hub adapter.

11 Claims, 4 Drawing Sheets

(56) References Cited

U.S. PATENT DOCUMENTS

| | | | |
|---|---|---|---|
| 4,646,722 | A | 3/1987 | Silverstein et al. |
| 5,170,774 | A | 12/1992 | Heckele |
| 5,176,645 | A | 1/1993 | Guerrero |
| 5,178,606 | A | 1/1993 | Ognier et al. |
| 5,199,417 | A | 4/1993 | Muller et al. |
| 5,207,213 | A | 5/1993 | Auhll et al. |
| 5,237,984 | A | 8/1993 | Williams et al. |
| 5,269,756 | A | 12/1993 | Dryden |
| 5,313,934 | A | 5/1994 | Wiita et al. |
| 5,354,267 | A | 10/1994 | Niermann et al. |
| 5,413,092 | A | 5/1995 | Williams, III et al. |
| 5,419,309 | A | 5/1995 | Biehl |
| 5,439,022 | A | 8/1995 | Summers et al. |
| 5,486,155 | A | 1/1996 | Muller et al. |
| 5,505,707 | A | 4/1996 | Manzie et al. |
| 5,551,448 | A | 9/1996 | Matula et al. |
| 5,554,112 | A | 9/1996 | Walbrink et al. |
| 5,556,258 | A | 9/1996 | Lange et al. |
| 5,575,756 | A | 11/1996 | Karasawa et al. |
| 5,630,795 | A | 5/1997 | Kuramoto et al. |
| 5,797,836 | A | 8/1998 | Lucey et al. |
| 5,989,183 | A | 11/1999 | Reisdorf et al. |
| 6,004,263 | A | 12/1999 | Nakaichi et al. |
| 6,110,103 | A | 4/2000 | Donofrio |
| 6,126,592 | A | 10/2000 | Proch et al. |
| 6,181,442 | B1 | 1/2001 | Ogura et al. |
| 6,282,442 | B1 | 8/2001 | DeStefano et al. |
| 6,354,813 | B1 | 3/2002 | Laing |
| 6,447,446 | B1 | 9/2002 | Smith et al. |
| 6,478,731 | B2 | 11/2002 | Speier et al. |
| 6,537,209 | B1 | 3/2003 | Pinkhasik et al. |
| 6,558,379 | B1 | 5/2003 | Batchelor et al. |
| 6,652,484 | B1 | 11/2003 | Hunckler et al. |
| 6,679,874 | B2 | 1/2004 | Miser |
| 7,252,110 | B2 | 8/2007 | Semeia |
| 7,270,647 | B2 | 9/2007 | Karpowicz et al. |
| 7,413,542 | B2 | 8/2008 | Kucklick et al. |
| 7,708,689 | B2 | 5/2010 | Deppmeier et al. |
| 7,758,497 | B2 | 7/2010 | Hem |
| 7,811,228 | B2 | 10/2010 | Adams |
| 8,001,984 | B2 | 8/2011 | Sasaki |
| 8,047,215 | B1 | 11/2011 | Sasaki |
| 8,079,952 | B2 | 12/2011 | Fujimoto |
| 8,197,400 | B2 * | 6/2012 | Boutillette ......... A61B 1/00128 285/145.2 |
| 8,231,574 | B2 | 7/2012 | Haack et al. |
| 8,337,470 | B2 | 12/2012 | Prasad et al. |
| 8,394,013 | B2 | 3/2013 | Ichimura |
| 8,419,624 | B2 | 4/2013 | James et al. |
| 8,475,362 | B2 * | 7/2013 | Sohn ................. A61B 1/00006 600/105 |
| 8,506,475 | B2 | 8/2013 | Brannon |
| 8,870,754 | B2 * | 10/2014 | Wood ..................... A61B 1/018 600/137 |
| 9,585,547 | B2 | 3/2017 | Cheng et al. |
| 2002/0103420 | A1 | 8/2002 | Coleman et al. |
| 2002/0120180 | A1 | 8/2002 | Speier et al. |
| 2004/0073088 | A1 | 4/2004 | Friedman et al. |
| 2005/0025646 | A1 | 2/2005 | Miller et al. |
| 2006/0041186 | A1 | 2/2006 | Vancaillie |
| 2006/0199998 | A1 | 9/2006 | Akui et al. |
| 2006/0264995 | A1 | 11/2006 | Fanton et al. |
| 2007/0149993 | A1 | 6/2007 | Kasahara et al. |
| 2007/0213668 | A1 | 9/2007 | Spitz |
| 2007/0238926 | A1 | 10/2007 | Boulais |
| 2008/0072970 | A1 | 3/2008 | Gasser et al. |
| 2008/0081948 | A1 | 4/2008 | Weisenburgh et al. |
| 2008/0200764 | A1 | 8/2008 | Okada |
| 2009/0234193 | A1 | 9/2009 | Weisenburgh, II et al. |
| 2009/0244223 | A1 | 10/2009 | Mizutani et al. |
| 2010/0198012 | A1 | 8/2010 | Poole et al. |
| 2011/0230716 | A1 | 9/2011 | Fujimoto |
| 2012/0316394 | A1 | 12/2012 | Yoshida et al. |
| 2013/0205936 | A1 | 8/2013 | Schmieding et al. |
| 2013/0211433 | A1 | 8/2013 | Kadykowski et al. |
| 2013/0289595 | A1 | 10/2013 | Edwards et al. |
| 2016/0143512 | A1 | 5/2016 | Cheng et al. |

FOREIGN PATENT DOCUMENTS

| | | |
|---|---|---|
| JP | H06/189893 A | 7/1994 |
| JP | 2005/040184 A | 2/2005 |
| JP | 2012/045325 A | 3/2012 |
| WO | 2002/033296 A2 | 4/2002 |
| WO | 2012/069592 A1 | 5/2012 |

OTHER PUBLICATIONS

Potentially Related Application, U.S. Appl. No. 14/497,815, dated Sep. 26, 2014.

Potentially Related Application, U.S. Appl. No. 14/493,581, dated Sep. 23, 2014.

Potentially Related Application, U.S. Appl. No. 14/496,473, dated Sep. 25, 2014.

Potentially Related Application, U.S. Appl. No. 14/493,700, dated Sep. 23, 2014.

Potentially Related Application, U.S. Appl. No. 14/551,208, dated Nov. 24, 2014.

Potentially Related Application, U.S. Appl. No. 14/592,397, dated Jan. 8, 2015.

"U.S. Appl. No. 14/551,440, Final Office Action dated Feb. 17, 2016", 12 pgs.

"U.S. Appl. No. 14/551,440, Final Office Action dated Aug. 19, 2016", 10 pgs.

"U.S. Appl. No. 14/551,440, Non Final Office Action dated May 10, 2016", 8 pgs.

"U.S. Appl. No. 14/551,440, Non Final Office Action dated Nov. 18, 2015", 8 pgs.

"U.S. Appl. No. 14/551,440, Notice of Allowance dated Nov. 1, 2016", 7 pgs.

"U.S. Appl. No. 14/551,440, Response filed Jan. 12, 2016 to Non Final Office Action dated Nov. 18, 2015", 13 pgs.

"U.S. Appl. No. 14/551,440, Response filed Mar. 31, 2016 to Final Office Action dated Feb. 17, 2016", 12 pgs.

"U.S. Appl. No. 14/551,440, Response filed Aug. 8, 2016 to Non Final Office Action dated May 10, 2016", 14 pgs.

"U.S. Appl. No. 14/551,440, Response filed Oct. 19, 2016 to Final Office Action dated Aug. 19, 2016", 15 pgs.

"U.S. Appl. No. 14/551,440, Response filed Nov. 4, 2015 to Restriction Requirement dated Oct. 27, 2015", 2 pgs.

"U.S. Appl. No. 14/551,440, Restriction Requirement dated Oct. 27, 2015", 6 pgs.

* cited by examiner

ADJUSTABLE ENDOSCOPE SHEATH

FIELD

The present teachings generally relate to an endoscope sheath and more specifically to an endoscope sheath that is at least partially rotatable relative to an endoscope.

BACKGROUND

Some endoscope sheaths include one or more features, such as a sheath tube tip, for cleaning a distal viewing end of an endoscope or for providing illuminating functions, viewing functions, or both to the distal viewing end of an endoscope and/or an internal location of a patient. To function properly, the sheath tube tip may need to be generally rotationally aligned with the distal viewing end of the endoscope, the internal location of the patient, or both. Some endoscope sheaths include a specific detail, such as an arms configured to engage another specific detail on the endoscope like a light post. This type of engagement not only provides a connection means between the endoscope sheath and the endoscope, but also rotationally aligns the sheath tube tip and the distal viewing end. However, in some instances, the position of the light post may vary, which may, accordingly, affect the rotational alignment between the sheath tube tip and the distal viewing end of the endoscope, the internal location of the patient, or both. For example, in some instances, the light post can extend from the endoscope in different directions (e.g. the light post can extend upwardly or downwardly from the endoscope), which may affect the rotational alignment between the sheath tube tip and the distal viewing end of the endoscope, the internal location of the patient, or both. In these instances, to achieve rotational alignment there between, various individual endoscope sheath configurations may be required for engaging various individual endoscope configurations which may undesirably increase endoscope sheath inventory, increase the space required to store the increased endoscope sheath inventory, and also increase the time required to prepare for a medical procedure, for example. In other instances, for example, depending on how a doctor holds the endoscope, the light post can be made to extend upwardly, downwardly, or in a different direction, which may also affect the rotational alignment of the sheath tube tip relative to the internal location of the patient. What is needed is a single endoscope sheath that can engage an endoscope with an upwardly extending light post, a downwardly extending light post, or a light post extending in a direction in between, while providing for the sheath tube tip to be rotationally adjusted relative to the distal viewing end of the endoscope, an internal location of a patient, or both. Some examples of endoscope sheaths can be found in U.S. Pat. Nos. 7,811,228, 5,554,112, and 5,797,836; U.S. Pat. Pubs. 2013/0205936 and 2002/0120180; and U.S. patent application Ser. Nos. 14/493,700 and 14/493,581, all of which are incorporated by reference herein in their entirety for all purposes.

SUMMARY

The present teachings provide a sheath tube extending along a longitudinal axis between a proximal end and a distal end, the sheath tube is configured to receive at least a portion of an endoscope; a hub connected to the proximal end of the sheath tube; and a hub adapter engaging the hub and configured to engage the endoscope, wherein the sheath tube can rotate about the longitudinal axis without rotation of the hub adapter, and wherein the sheath tube is restricted from moving axially along the longitudinal axis relative to the hub adapter.

The present teachings also provide a method comprising providing a sheath tube extending along a longitudinal axis between a proximal end and a distal end; providing a hub connected to the proximal end of the sheath tube; providing an endoscope having a proximal end, a distal end and a shoulder located there between; providing a hub adapter between the hub and the shoulder, the hub adapter including an arm; inserting at least a portion of the endoscope through the hub adapter and into the sheath tube; engaging a proximal end of the hub adapter against the shoulder so that the arm engages a light post extending from the endoscope; engaging the hub with a distal end of the hub adapter; and rotating the sheath tube about the longitudinal axis until the proximal end of the sheath tube is aligned with the endoscope.

The present teachings solve one or more of the current problems by providing a single endoscope sheath that can engage an endoscope with an upwardly extending light post, a downwardly extending light post, or a light post extending in a direction there between, while providing for the distal tip of the endoscope sheath to be rotationally adjusted relative to the distal viewing end of the endoscope, an internal location of a patient, or both.

DETAILED DESCRIPTION

Figure 1:
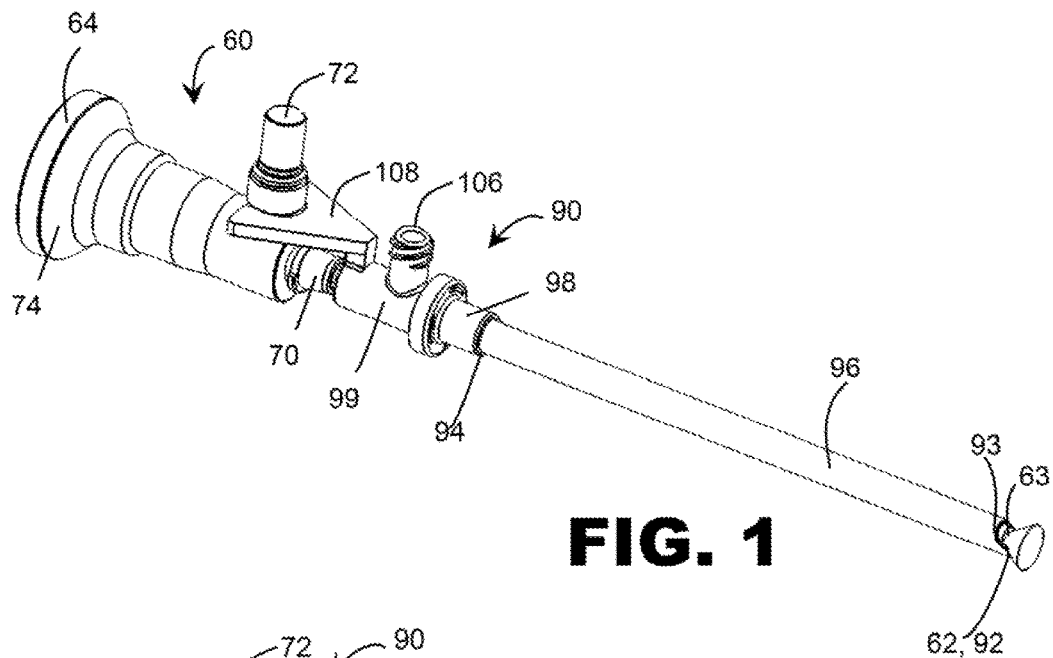
FIG. 1 illustrates a perspective view of an endoscope inserted or received into an endoscope sheath in accordance with the teachings herein.

The explanations and illustrations presented herein are intended to acquaint others skilled in the art with the teachings its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such c alms are entitled. The disclosures of all articles and references, including patent applications and publications, are incorporated by reference for all purposes. Other combinations are also possible as will be gleaned from the following claims which are also hereby incorporated by reference into this written description.

The present teachings provide a system and an endoscope sheath for use with an endoscope. The system may function to clean and protect an endoscope sheath, an endoscope, or both. The system may function to clean and protect a distal end of an endoscope. The system may function to clean an image sensor, a lens, or a device located at a distal viewing end of an endoscope. The system may include one or more irrigation sources supplying an irrigation fluid to an endoscope sheath, an endoscope, a distal viewing end of an endoscope, or a combination thereof, and one or more suction sources pulling suction from an endoscope sheath, an endoscope, a distal viewing end of an endoscope, or a combination thereof. The one or more irrigation sources, suction sources, or both may be in constant communication, selective communication, or both with an endoscope sheath, an endoscope, a distal viewing end of an endoscope, or a combination thereof. The system may include one or more control modules that may function to control the one or more irrigation sources, suction sources, endoscope sheaths, endoscopes, or a combination thereof.

The one or more control modules may function to control an amount of irrigation fluid, suction, or both supplied, applied, or pulled to/from an endoscope sheath, an endoscope, a distal viewing end of an endoscope, an area or location of interest, a surgical site, or a combination thereof. The one or more control modules may control a running speed, pumping duration, or both of the one or more pumps supplying irrigation fluid. The one or more control modules may control an order of application of irrigation fluid, suction, or both. The one or more control modules may function to stop a flow of irrigation fluid or suction, apply a flow of irrigation fluid or suction, or a combination thereof. The one or more control modules may include a power source, which may be electricity, battery, or both. The one or more control modules may include a microprocessor, a computer, a control algorithm, or a combination thereof. The one or more control modules may include one or more user interfaces, one or more pumps, one or more valves, or a combination thereof.

The one or more user interfaces may function to provide a user, such as a surgeon, doctor, or nurse, with the ability to monitor and/or control the system. The user interface may include one or more control knobs, buttons, switches, or selectors; one or more indicators; one or more user controls; one or more devices for adjusting, changing, or setting a system parameter or function; or a combination thereof. During use, for example, a user may activate, adjust, or both one or more of the control knobs, buttons, indicators, controls, etc. to activate, control, adjust or a combination thereof one or more pumps, valves, system functions, or a combination thereof to start, stop, or change a system function, such as an irrigation function, a suction function, or application cycle.

The one or more pumps may function to supply, circulate, or move irrigation fluid from an irrigation source to a control module, an endoscope sheath, an endoscope, a distal viewing end of an endoscope, or a combination thereof. The pump may supply, circulate, or move irrigation fluid with an impeller. The pump may function to create a negative pressure (e.g., suction or vacuum). Preferably, when the pump is activated an amount of irrigation fluid is moved, which, during use, may be constant or may selectively vary. The pump may be a lobe pump, a centrifugal pump, a positive displacement pump, a rotary positive displacement pump, a diaphragm pump, a peristaltic pump, a rope pump, a gear pump, a screw pump, a progressing cavity pump, a roots-type pump, a plunger pump, or a combination thereof. Preferably, the pump is a peristaltic pump for supplying irrigation fluid through one or more irrigation lines.

The irrigation fluid may function to clean an endoscope sheath, an endoscope a distal viewing end of an endoscope, or a combination thereof. The irrigation fluid may function to move or flush particles opaque fluids, contaminants, cut biological tissue, blood, obstructions, etc. or a combination thereof from an endoscope sheath, an endoscope, a distal viewing end of an endoscope, a surgical site, or a combination thereof. The irrigation fluid may function to clean an image sensor, lens or device of an endoscope while the endoscope and endoscope sheath is in a patient. The irrigation fluid may be bioabsorbable. During an application cycle, the irrigation fluid may be applied, continuously, selectively, intermittingly, on-demand, or a combination thereof. The irrigation fluid may be supplied with a pump configured to pump the irrigation fluid at a pressure. The pressure of the irrigation fluid may change as the irrigation fluid reaches a distal end of an endoscope sheath, an endoscope, a distal viewing end of an endoscope, or a combination thereof. The irrigation fluid may be supplied via a gravity feed, and thus, the pressure of the irrigation fluid may be determined by the height of an irrigation source. For example, a vertical placement height of an irrigation source may determine the amount of pressure and/or force the irrigation fluid applies to a distal end of an endoscope sheath, an endoscope, a distal viewing end of an endoscope, or a combination thereof. It may be desirable that the pressure of the irrigation fluid is sufficiently high so that a flow director may redirect the irrigation fluid. The flow director may be located at a distal end of the endoscope sheath. The irrigation fluid may be applied with a sufficient amount of pressure so that the surface tension of the irrigation fluid wicks across a distal end of an endoscope sheath, an endoscope, a distal viewing end of an endoscope, or a combination thereof (e.g., the pressure may be low enough that the irrigation fluid remains in contact with an endoscope sheath, an endoscope, or both). Preferably, the pressure is low so that the flow of irrigation fluid is laminar across an endoscope sheath, an endoscope, an image sensor, lens or device, or combination thereof. The irrigation fluid may be applied with a pressure of about 0.10 MPa or more, about 0.20 MPa or more, about 0.30 MPa or more, or even about 0.50 MPa or more. The irrigation fluid may be applied with a pressure of about 3 MPa or less, about 2 MPa or less, about 1 MPa or less, or even about 0.75 MPa or less. The pressure of the irrigation fluid may be varied based on a size, length, or both of an irrigation line extending between an irrigation source and an endoscope sheath, an endoscope, distal viewing end of an endoscope, or a combination thereof.

The one or more irrigation lines may function to connect an irrigation source to an endoscope sheath, endoscope, or both. The one or more irrigation lines may be one or any number of lines supplying irrigation fluid to an endoscope sheath, endoscope, or both. The one or more irrigation lines may function to assist in creating a pressure head so that the irrigation fluid is supplied, applied, transferred, moved, or a combination thereof to move, remove, or flush particles, opaque fluids, contaminants, cut biological tissue, blood, obstructions, or a combination thereof from a point of interest, an endoscope sheath, an endoscope, a distal viewing end of an endoscope, a surgical site, or from a combination thereof. The one or more irrigation lines may be elongated, rigid, flexible, or movable tubes or conduits, or a combination thereof. The one or more irrigation lines may be made of a material suitable for use in surgical procedures. The one or more irrigation lines may also connect a suction source to an endoscope sheath an endoscope, or both (i.e., suction may be supplied through the irrigation lines).

The suction source may function to move, remove, or flush particles, opaque fluids, contaminants, cut biological tissue, blood, obstructions or a combination thereof from a point of interest, an endoscope sheath, an endoscope, a distal viewing end of an endoscope, a surgical site, or from a combination thereof. The suction source may function to perform a drying function, remove fluid spots, remove contaminants, or a combination thereof. The suction source may be a pump, reversal of a motor, a common suction source, a hospital suction source, or a combination thereof. The suction source may be configured to pull a sufficient amount of vacuum through one or more suction lines, irrigation lines, or both to remove a predetermined amount of fluid in a predetermined amount of time. For example, the suction source may pull suction so that 10 ml of irrigation fluid is removed in 1 to 2 seconds. The suction source may pull suction that is continuous, selective, on-demand, or a combination thereof through one or more suction lines.

The one or more suction lines may function to connect a suction source to an endoscope sheath, an endoscope, or both. The one or more suction lines may be one or more lines providing a conduit for suction or vacuum to be pulled by, suction source from an endoscope sheath, an endoscope, a distal viewing end of an endoscope, or a combination thereof. The one or more suction lines may function to assist in pulling a vacuum at or near a distal end of an endoscope sheath, an endoscope, a distal viewing end of an endoscope, or a combination thereof. The one or more suction lines may be elongated, rigid, flexible, movable tubes conduits, or a combination thereof. The one or more suction lines may be made of a material suitable for use in surgical procedures to pull vacuum or suction. The one or more suction lines may also connect an irrigation source to an endoscope sheath, an endoscope, or both (i.e., irrigation may be supplied through the suction lines). The suction lines and the irrigation lines may be the same line or may be different lines. The suction line the irrigation line, or both may include one or more valves, fittings, or both.

The one or more valves may function to allow either a suction function or an irrigation function to work at a given time. For example, the one or more valves may function to block one or more of the irrigation lines or one or more of the suction lines so that only suction or only irrigation fluid, respectively, is applied at a given time. The one or more valves may be a check valve, a back flow preventers or both. The one or more valves may be located proximate to an endoscope sheath, an endoscope, an irrigation source, a suction source, a control module, or a combination thereof. If more than one valve is present, the valves may be connected electrically, hydraulically, fluidly, or in a combination thereof. For example, when one valve is opened another valve can be closed. If two or more valves are present, the valves may be operated in a sequence (e.g., one valve opens and closes before another valve opens); operated simultaneously (e.g. both valves open at the same time); operated on a delay (e.g. one valve opens or closes before another valve opens or closes); or in any combination thereof. The one or more valves may be part of, or in communication with, a common fitting, located proximate to a common fitting, or both.

The one or more common fittings may function to connect one or more suction lines, irrigation lines, or both to a common line. The one or more common fittings may function to provide suction and irrigation fluid to an endoscope sheath, endoscope, or both through a single port on the endoscopes sheath or endoscope. For example, the common fitting may connect a suction line and an irrigation line to a common line that is connected to an endoscope sheath so that irrigation fluid can be supplied to the endoscope sheath and after the irrigation fluid is supplied, suction may be applied through the same line. The one or more common fittings may connect a one or more suction lines, irrigation lines, or both, to multiple devices so that the multiple devices may be used simultaneously, in series, in parallel, or in a combined use. The one or more common fittings may include two or more openings, three or more openings, four or more openings, or five or more openings. Each opening may receive one or more suction lines, one or more irrigation lines, or both and may fluidly connect the one or more lines together. More than one common fitting may be used to connect multiple lines together. For example, a first common fitting with three openings may be connected to a second common fitting with three openings so that two lines are connected to one opening of the first common fitting and one tube is connected to each of the other two openings. Preferably, the common fitting is generally "Y" shaped and two of the openings lead into a third opening that is connected to one or more commons line and/or one or more delivery lines.

The one or more common lines and/or one or more delivery lines may function to deliver, supply, apply, remove or a combination thereof irrigation fluid, suction, or both to an endoscope sheath, an endoscope, or both. The common line may function to provide a combination of multiple different fluids, devices, suction levels, fluid pressures, or a combination thereof. The common line may provide a single access point between an irrigation source, a suction source, a control module, or a combination thereof and an endoscope sheath, an endoscope, or both. The common line may have an increased cross-sectional area (e.g., diameter) relative to a cross-sectional area of an irrigation line, a suction line, or both. The common line may be the same size as the irrigation lines, suction lines, or both. The common line may extend between a common fitting and a port of an endoscope sheath, an endoscope, or both. The common line may function to deliver one or more fluids to an endoscope sheath, an endoscope, or both during an application cycle.

The application cycle may function to clean, protect or both an endoscope sheath, an endoscope, a distal viewing end of an endoscope, an area or location of interest, a surgical site, or a combination thereof. The application cycle may function to clean an imaging lens or device associated with or located at a distal viewing end of an endoscope. The application cycle may be sufficiently long so that an image sensor, a lens or device of an endoscope, a distal viewing end of an endoscope, or a combination thereof can be cleaned and good images can be obtained therewith. The application cycle may be a cycle where a one or a combination of different applications, cycles, sequences, and/or functions are applied or performed. The application cycle may be a cycle where irrigation fluid and suction are applied simultaneously, in sequence, intermittingly, on-demand, or in a combination thereof, to clean, protect or both an endoscope sheath, an endoscope, a distal viewing end of an endoscope, or a combination thereof. For example, an application cycle may include an application of irrigation fluid followed immediately by an application of suction. The application cycle may apply a concurrent application of irrigation fluid and suction. The application cycle may include only an application of irrigation fluid (i.e., a flushing cycle, a washing manner, etc.) with no suction. The application cycle may include only an application of suction with no application of irrigation fluid. The application cycle may be varied, adjusted, monitored, and/or controlled by a user, by one or more control modules, user interfaces, or a combination thereof. For example, a user may pre-set an application cycle so that one touch of a switch causes irrigation fluid to run for 5 seconds.

The endoscope may function to provide a surgeon, a doctor, a nurse, or other interested persons with visual access into a remote location, such as an internal location of a patient. The endoscope may be used in non-invasive surgery. The endoscope may be used for orthoscopic surgery. The endoscope may be inserted into an incision in tissue. The endoscope may be inserted into an orifice, such as an ear, nose, throat, rectum, or urethra. The endoscope may have a generally circular cross section. The endoscope may include a tubular section that is generally elongated and generally cylindrical. The tubular section may extend along a longitudinal axis toward a distal viewing end. The endoscope may include a hand piece extending toward a proximal end of the endoscope. The hand piece may include a shoulder engaging a knob. The hand piece may be gripped by a user. The tubular section may be inserted into an endoscope sheath, a sheath tube, or both. The tubular section may include one or more image sensors, lenses, or devices. The one or more image sensors, lenses, or devices may be located at a distal viewing end of the endoscope. The one or more image sensors, lenses, or devices may function to provide, images that are black and white, color, thermal, or a combination thereof. The one or more image sensors, lenses, or devices may be located at an angle. For example, the angle of the one or more image sensors, lenses, or devices may be about 0°, 20°, 30°, 45°, 60°, 70°, or a combination thereof. The endoscope may include a distal end, a distal viewing end, or both.

The distal viewing end may be the distal end of the endoscope, the tubular section, or both may be inserted into an incision in tissue of a patient, a naturally occurring orifice, or both so that a feature of interest can be viewed using a minimally invasive means. Accordingly, the distal viewing end of the endoscope may be the leading portion of the endoscope (i.e., the first portion entering a patient). The distal viewing end of the endoscope may include the one or more image sensors, lenses, or devices. The distal viewing end of the endoscope may include a viewing cone or an area extending outwardly therefrom for viewing an area or location of interest. The distal viewing end may be moveable, variable, adjustable, or a combination thereof. The distal viewing end of the endoscope may be configured to be rotationally aligned with a distal end of an endoscope sheath, a sheath tube tip, or both. The distal end of the endoscope may oppose a proximal end of the endoscope.

The proximal end of the endoscope may function to be held or gripped by a user. The proximal end of the endoscope may function to provide controls to a doctor, a surgeon, a nurse, or other interested persons. The proximal end of the endoscope may function to provide power controls, sensing controls, irrigation controls, suction controls, a connection point to/for outside devices, or a combination thereof. The proximal end of the endoscope may provide an interface for connecting other functional components to the endoscope, such as an imaging device (e.g., a camera). The proximal end of the endoscope may include a hand piece. During use, the proximal end of the endoscope may be retained out of a patient while a distal end of the endoscope is in the patent. The proximal end of the endoscope may include a visual port.

The visual port may function to provide a viewing area or window for observing a feature of interest located at or near a distal viewing end of the endoscope. The visual port may be an optical window. The visual port may function to provide an output so that an image can be displayed on a monitor. The visual port may include a connector or a plug for connecting to a display monitor. The visual port may be integrally formed with the endoscope. The visual port may be removeably coupled to the proximal end of the endoscope via a threaded engagement. A shoulder may be located between the proximal and distal ends of the endoscope.

The shoulder may function to prevent a proximal end of the endoscope from entering a patient. The shoulder may be a distal or terminal portion of a proximal end of the endoscope, a hand piece, or both. The shoulder may be generally vertical, generally flat, or generally orthogonal relative to a longitudinal axis of a sheath tube. Once an endoscope is at least partially received into an endoscope sheath, the shoulder may function to restrict or prevent the sheath tube from moving towards a proximal end of the endoscope. The shoulder may function to form a connection with a hub adapter. The shoulder may include an undercut, one or more ribs, a projection, a flange, or a combination, thereof engaging a hub adapter. The shoulder may form a snap-fit connection, a press-fit connection, a removable connection, a secure connection, an, abutting connection, a line-to-line connection, or a combination thereof with a flare of a hub adapter. One or more light posts may be located between the shoulder and a proximal end of the endoscope.

The one or more light posts may function to direct or provide light from a light source to, or into an endoscope, an endoscope sheath, or both so that a feature of interest located at or near a distal viewing end of an endoscope can be illuminated. The one or more light posts may include a plug or a connector for connecting a light source. The light source may be a light waveguide, an optical illuminator, a fiber optic, or a combination thereof. The one or more light posts may project or extend from the endoscope upwardly, downwardly, or in a direction there between relative to a longitudinal axis of the endoscope. The one or more light posts may be integrally formed with the endoscope. The one or more light posts may be connected to the endoscope. The one or more light posts may be made of metal, plastic, a biocompatible material, or a combination thereof. The one or more light posts may be configured to be engaged by the endoscope sheath. The one or more light posts may be engaged by an arm of an endoscope sheath, an arm of a hub adapter, or both. The one or more light posts may include a recess to be engaged by an arm, a yoke, or both. The one or more light posts may be engaged by an arm, a yoke, or both to help restrict or prevent rotation of a hub adapter, a sheath tube, or, both relative to a longitudinal axis of the sheath tube.

The endoscope sheath may function provide one or more conduits, lumen, channels, or a combination thereof, for irrigation devices, suction devices, surgical tools, other functional device (e.g., a cutting tool, cauterizing tool, or both) or a combination thereof to extend into or out of a distal end of thereof. The endoscope sheath may function to provide protective functions, cleaning functions, washing functions, or a combination thereof to an endoscope, a surgical tool or device, a functional device, or a combination thereof. The endoscope sheath may function to clean and protect a distal viewing end of an endoscope. The endoscope sheath may include a sheath tube.

The sheath tube may function to clean and protect an endoscope. The sheath tube may create one or more conduits for providing irrigation fluid, suction, or both to a distal end of the endoscope. The sheath tube may function to receive, engage, protect, clean, or a combination thereof a distal viewing end of an endoscope. The sheath tube may include one or more through holes or bores extending along a longitudinal axis between a proximal end and a distal end. The sheath tube may be fabricated from a material suitable for use in medical procedures. The sheath tube may include one or more positioning devices. The sheath tube may be generally the same size and shape as an endoscope, a tubular section of an endoscope, or both, or slightly larger. For example, if tubular section of an endoscope has a generally circular cross section, then the sheath tube may also have a generally circular cross section. The sheath tube may have a shape that is different from an endoscope. The sheath tube may be any shape configured to receive, engage, support, or a combination thereof an endoscope, one or, more irrigation devices, one or more suction devices, one or more surgical tools or devices, one or more other functional devices, or a combination thereof. The sheath tube may have a uniform wall thickness, a variable wall thickness, or both. The sheath tube may function to locate, support, position, or a combination thereof an endoscope, a distal viewing end of an endoscope, one or more irrigation devices, one or more suction devices, one or more surgical tools, one or more other functional device, or a combination thereof. The sheath tube may include one or more positioning devices. The one or more positioning devices may position an endoscope within the sheath tube so that the endoscope and the sheath tube are concentric, or offset. The sheath tube may be selectively moved and adjusted relative to the shoulder of the endoscope. The one or more sheath tubes may be rotationally moved about its longitudinal axis so that the sheath tube tip located at a distal end of the sheath tube can be rotationally aligned with a distal viewing end of the endoscope. When the sheath tube and the sheath tube tip are rotated, the endoscope may not rotate.

The sheath tube tip may be the distal end of the sheath tube. The sheath tube tip may function to engage an endoscope, a distal end of an endoscope, a lens or imaging device, or a combination thereof. The sheath tube tip may function to direct irrigation fluid, suction, or both, across a distal end of an endoscope sheath, a distal viewing end of an endoscope, or both. The sheath tube tip may act as a distal end stop so that a distal viewing end of an endoscope is restricted or prevented from passing through the distal end of the endoscope sheath. The sheath tube tip may be open, or may function to selectively open, remain open, or both so that irrigation fluid can exit the sheath tube. The sheath tube tip may be configured to not interfere with imaging capabilities of the endoscope. The sheath tube tip may function to direct a viewing cone of an endoscope. The sheath tube tip may include an angled tip. The sheath tube tip may extend from a distal end of the sheath tube at an angle that substantially matches an angle of a viewing cone. For example, the sheath tube tip may include an angle on the order of 30-degrees, 45-degrees, 90-degrees etc. The sheath tube may be selectively moved so that the sheath tube tip can be rotationally aligned with the distal viewing end of the endoscope. When the sheath tube is rotated about its longitudinal axis, the sheath tube correspondingly rotates. A hub may engage a proximal end of the sheath tube.

The hub may function to connect the sheath tube to a hub adapter. The hub may cooperate with the hub adapter and function to restrict or prevent the sheath tube from axially moving along a longitudinal axis of the sheath tube, while allowing the sheath tube to rotate about the longitudinal axis of the sheath tube. The hub may be fabricated from a material suitable for use in medical procedures. The hub may include a through bore so that at least a portion of the endoscope sheath can be received through the hub when the endoscope is received or inserted into the sheath tube. A distal end of the hub may be fixedly connected or removeably connected to the sheath tube with one or more mechanical fasteners, such as adhesives, threads, snap fits, one or two-way connection systems, a series of ribs, or a combination thereof. A distal end of the hub may be over molded over a proximal end of a sheath tube or integrally formed therewith. A proximal end of the hub may include a channel. The channel may engage a mating flange located at a distal end of the hub adapter. A proximal end of the hub may include a flange. The flange may engage a mating channel located at a distal end of the hub adapter.

The hub adapter may engage the hub and the endoscope and may function to restrict or prevent the sheath tube from axially moving along a longitudinal axis of the sheath tube, while allowing the sheath tube to rotate about the longitudinal axis of the sheath tube. The hub adapter may include a through bore for receiving at least a portion of the endoscope when the endoscope is received or inserted in to the sheath tube. At its proximal end, the hub adapter may include a flare engaging the shoulder of the endoscope. At its distal end, the hub adapter may include a flange. The flange may engage a mating channel located at a proximal end of the hub. At it distal end, the hub adapter may include a channel. The channel may engage a mating flange located at a proximal end of the hub.

The channel located on one of the hub and the hub adapter may cooperate with the flange located on the other of the hub and the hub adapter to form a rotational engagement there between. The channel may be formed from one or more radial projections. The channel may include one or more radial notches configured to receive one or more radial projections of the flange. The channel may include two or more notches, preferably three or more notches, four or more notches, or even five or more notches. The channel may include one or more radial projections configured to cooperate with one or more radial projections of the flange to axially secure the hub and the sheath tube with the hub adapter. That is, once the projections of the flange are received into the notches of the channel and the sheath tube and hub are rotated about the longitudinal axis of the sheath tube, the flange projections of the flange and projections of the channel may cooperate to prevent axial separation of the sheath tube relative and the shoulder, while allowing rotational movement there between. The channel may include two or more radial projections, preferably three or more radial projections, four or more radial projections, or even five or more radial projections. The channel may include one or more detents, projections, alignment features, or a combination thereof cooperating with the mating flange so that a rotational registration between the sheath tube and the endoscope can be controlled. In this regard, the rotational registration between the sheath tube and the endoscope can be restricted to select orientations, such as 45 degrees 60 degrees, 90 degrees 135 degrees 180 degrees etc.

The flange located on one of the hub and the hub adapter may cooperate with the channel located on the other of the hub and the hub adapter to form a rotational engagement there between. The flange may include one or more radial projections configured to be inserted or received into mating radial notches of the channel. The one or more radial projections of the flange may cooperate with one or more radial projections of the channel to axially secure the hub adapter and the endoscope to the hub and the sheath tube while allowing rotational movement there between. The flange may rotate within channel about the longitudinal axis of the sheath tube but may be restricted from axially separating or moving along the longitudinal axis of the sheath tube. The flange may include one or more detents, projections, alignment features, or a combination thereof cooperating with the channel so that a rotational registration between the sheath tube and the endoscope can be controlled. The hub adapter may include one or more arms engaging the endoscope or a light post of the endoscope.

The one or more arms may function to prevent rotation of the hub adapter relative to the endoscope, the sheath tube, or both. The one or more arms may cantilever from the hub adapter. The one or more arms may engage an endoscope, a light post of an endoscope or both. The one or more arms include a yoke at least partially surrounding and engaging the light post. The one or more arms or yoke may engage a notch or recess in the light post. A port may be located next to the one or more arms on the hub adapter.

The port of the hub adapter may function to receive irrigation fluid, suction, or both from an irrigation source, a suction source, a control module, or a combination thereof. The port may function to direct irrigation fluid, section, or both to an endoscope, a distal viewing end of an endoscope, a sheath tube, or a combination thereof. The port may be configured to engage a common line, a common fitting, a valve, or combination thereof to selectively supply irrigation food, section, or both to the hub adapter, the endoscope sheath, the endoscope, or a combination thereof.

FIG. 1 illustrates an endoscope 60 inserted into or received by an endoscope sheath 90. The endoscope 60 includes a visual port 74 located at a proximal end 64 for viewing a feature of interest located at or near a distal viewing end 62 thereof. The endoscope 60 includes a shoulder 70 located between the proximal and distal ends 64, 62. A light post 72 for connecting or providing illumination to the endoscope 60, the endoscope sheath 90, or both is located between the proximal end 64 and the shoulder 70. The endoscope sheath 90 includes a sheath tube 96 having a sheath tube tip 93 located at a distal end 92 of the sheath tube 96. A hub 98 is connected to a proximal end 94 of the sheath tube 96. A hub adapter 99 is located between the hub 98 and the shoulder 70 of the endoscope 60. The hub adapter 99 includes an arm 108 engaging the light post 72 of the endoscope 60 and a port 106 receiving irrigation fluid, suction, or both.

Figure 2A:
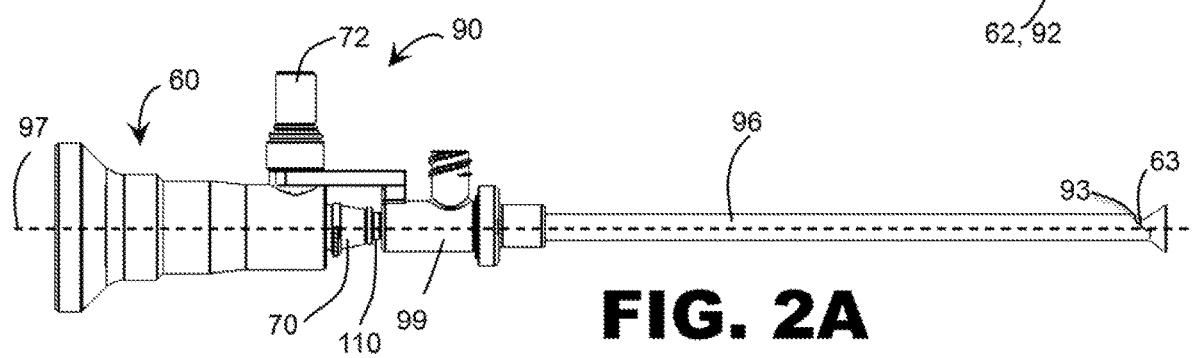
FIG. 2A illustrates a side view of an endoscope inserted or received into an endoscope sheath in accordance with the teachings herein; the endoscope is shown with an upwardly extending light post.

FIG. 2A illustrates an endoscope 60 inserted into or received by an endoscope sheath 90. The light post 72 is shown extending upwardly from the endoscope 60 relative to a longitudinal axis 97 of the sheath tube 96. The sheath tube tip 93 is oriented in the same general direction as the upwardly extending light post 72 and the distal viewing end 63 of the endoscope 60. The hub adapter 99 includes a flare 110 engaging the shoulder 70 of end endoscope 60.

Figure 2B:
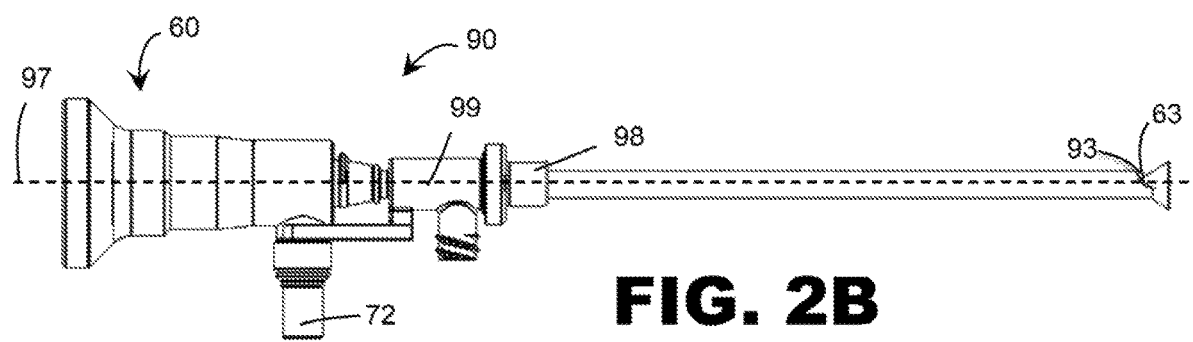
FIG. 2B illustrates a side view of an endoscope inserted or received into an endoscope sheath in accordance with the teachings herein; the endoscope is shown with a downwardly extending light post.
Figure 3A:
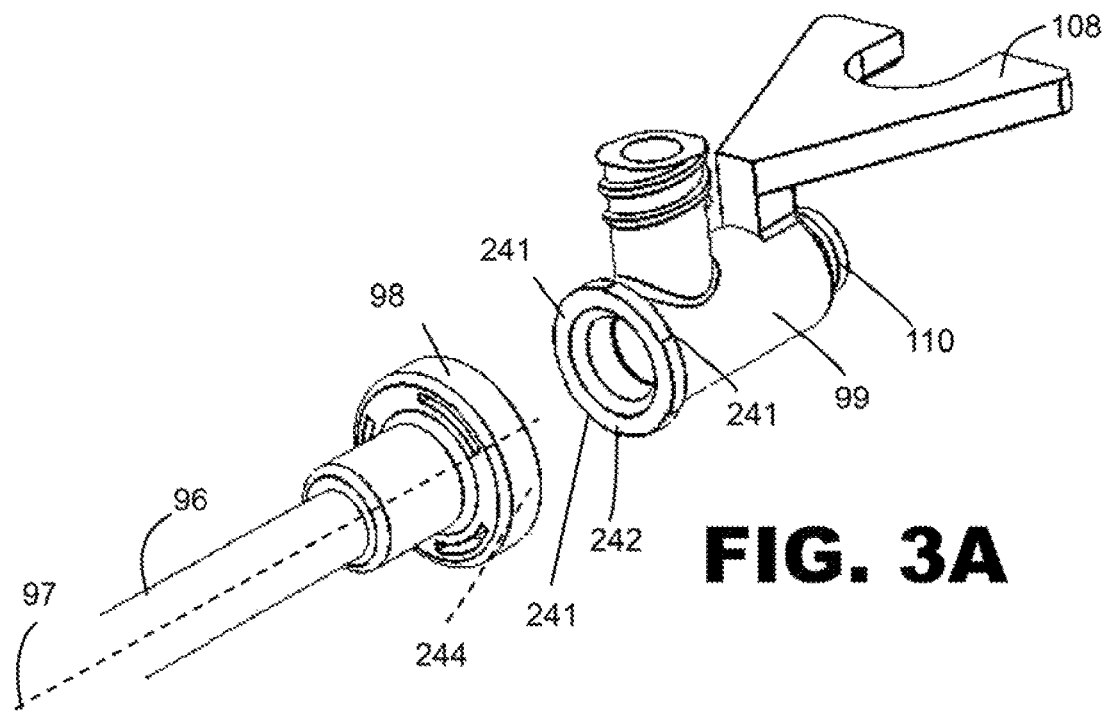
FIG. 3A illustrates a partial perspective exploded view of a sheath tube, a hub, and a hub adapter in accordance with the teachings herein.
Figure 3B:
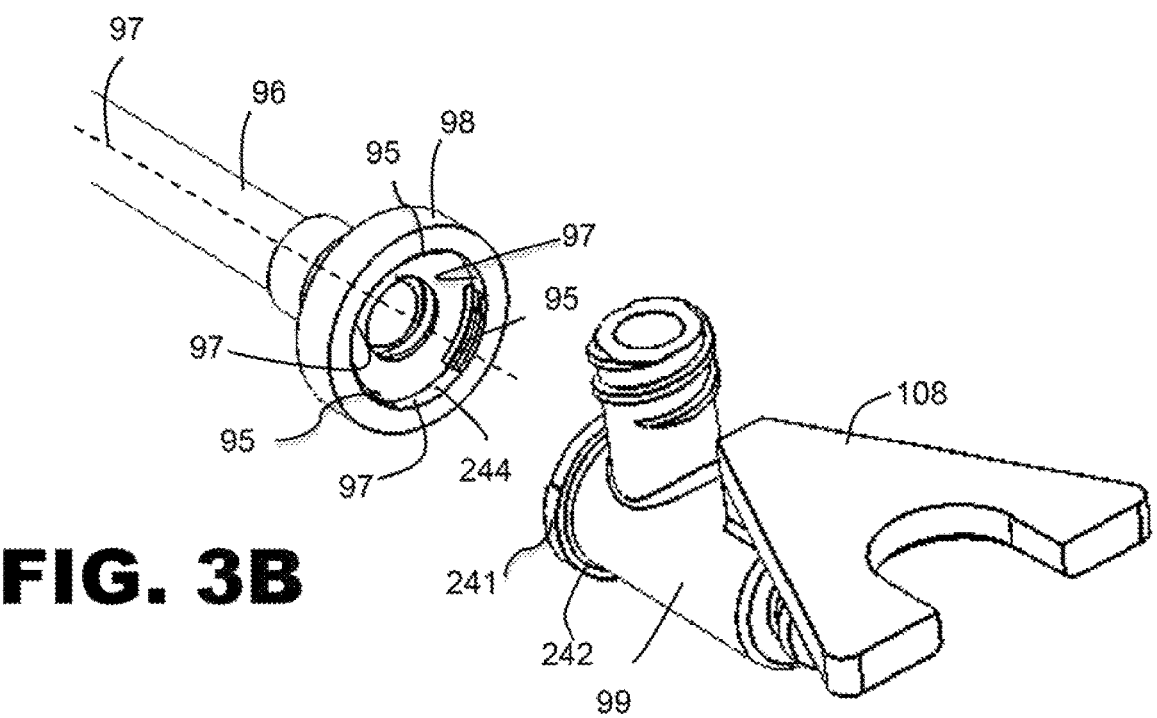
FIG. 3B illustrates a partial perspective exploded view of a sheath tube, a hub, and a hub adapter in accordance with the teachings herein.
Figure 4:
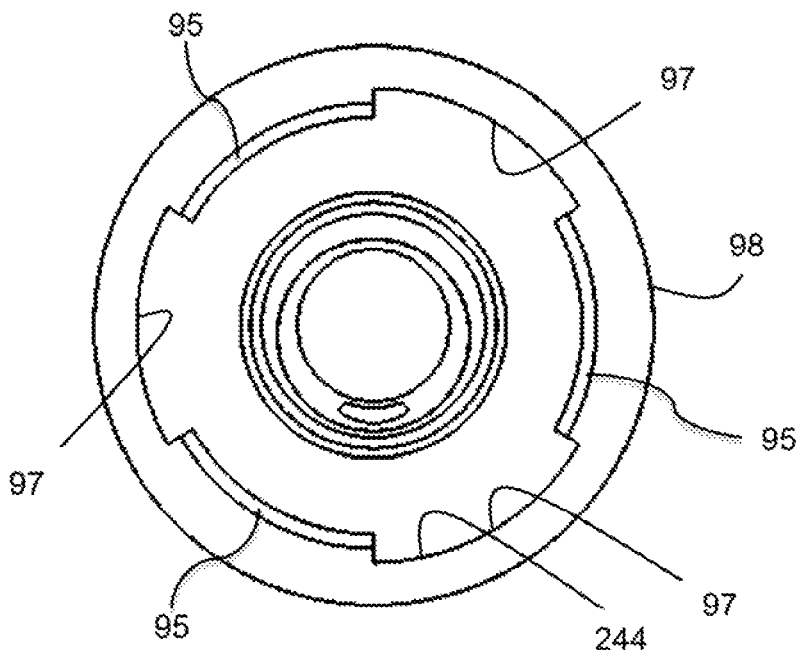
FIG. 4 illustrates a front view of a hub in accordance with the teachings herein.
Figure 5:
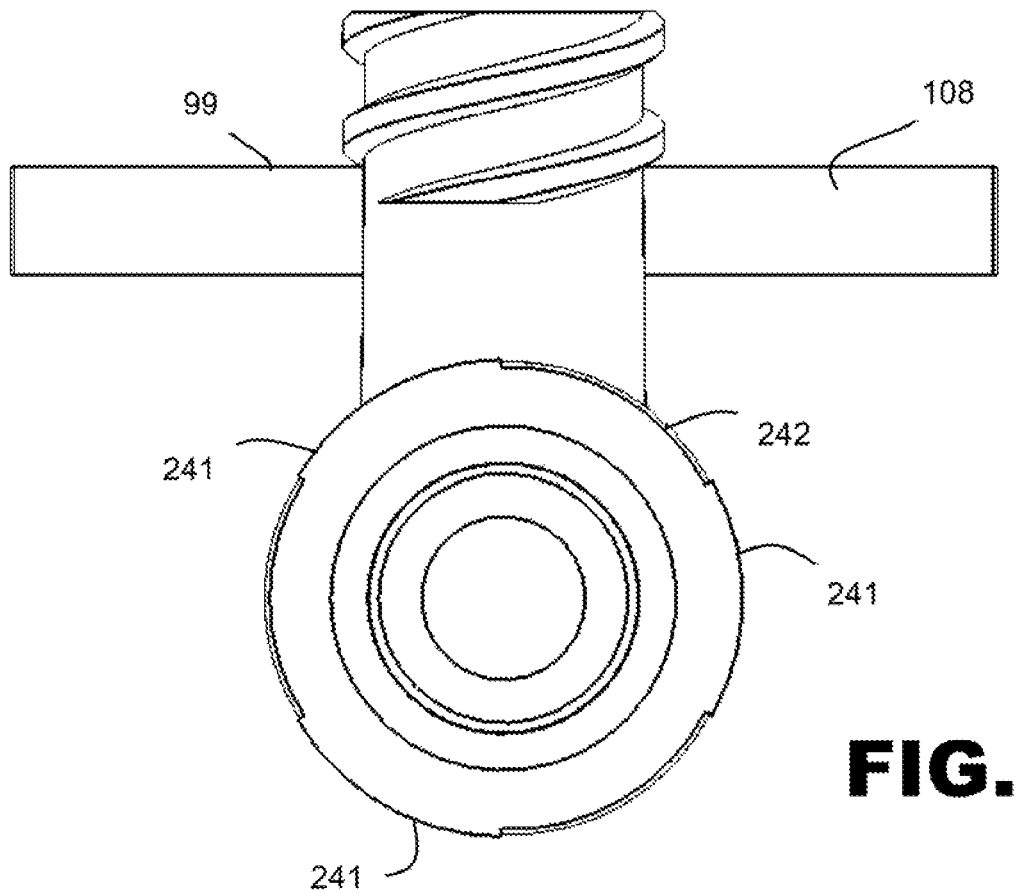
FIG. 5 illustrates a front view of a hub adapter in accordance with the teachings herein.

FIG. 2B illustrates an endoscope 60 inserted into or received by an endoscope sheath 90. The features of the endoscope 60 and endoscope sheath 90 are generally the same as those described in FIGS. 1 and 2A, except that the light post 72 is shown extending downwardly relative to the longitudinal axis 97 of the sheath tube 96, while the sheath tube tip 93 is shown positioned in the same general orientation of FIG. 2A. In this regard, the sheath tube tip 93 is oriented generally opposite the light post 72, but in the same general orientation as the distal viewing end 63 of the endoscope 60. The engagement between the hub 98 and the hub adapter 99 shown and described in the FIGS. 3A-5 provides for the sheath tube tip 93 to be selectively rotationally oriented relative to the light post 72 and the distal viewing end 63.

FIGS. 3A, 3B, 4 and 5 illustrate various views of the hub 98 and the hub adapter 99. The hub adapter 99 includes a flange 242 located generally opposite the flare 110. The flange 242 rotationally engages a channel 244 in the hub 98. The flange 242 includes a first series of radial projections 241 received into a series of mating radial notches 97 in the channel 244. The channel 244 includes a second series of radial projections 95 cooperating with the first series of radial projections 241 of the flange 241 to restrict the hub 98 and the sheath tube 96 from axially moving along the longitudinal axis 97 of the sheath tube 96 relative to the hub, adapter 99, while allowing the hub 98 and the sheath tube 96 to rotate about the longitudinal axis 97 relative to the hub adapter 99. The hub 98 and the sheath tube 96 can be separated from the hub adapter 99 and the endoscope 60 by aligning the first series of radial projections 241 of the hub adapter 99 with the series of mating radial notches 97 in the hub 98 and axially separating the sheath tube 96 from the endoscope 60.

Figure 6:
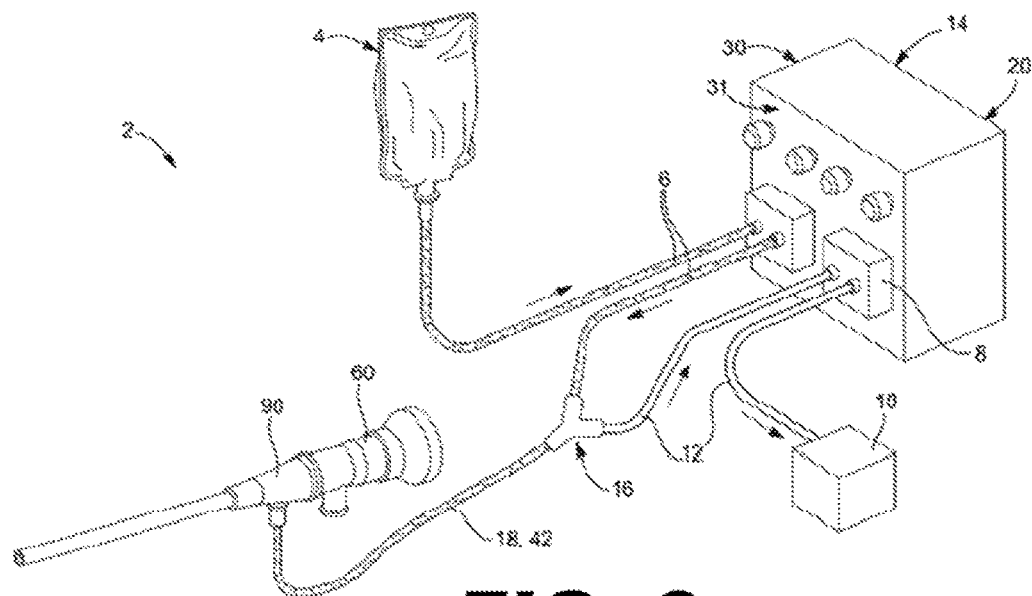
FIG. 6 illustrates a system for use with the endoscope and endoscope sheath of the teachings herein in accordance with the teachings herein.
Figure 7:
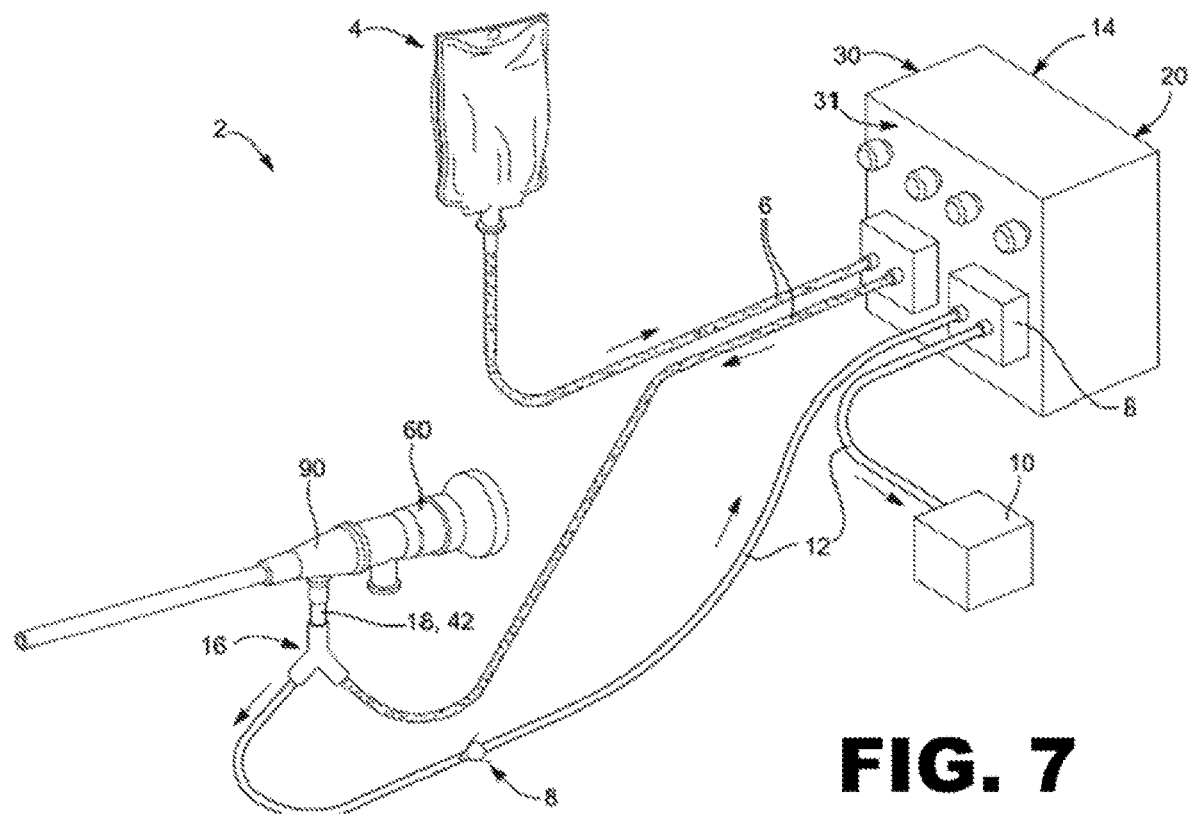
FIG. 7 illustrates a system for use with the endoscope and endoscope sheath of the teachings herein in accordance with the teachings herein.

FIGS. 6 and 7 illustrate an endoscope cleaning system 2. The endoscope cleaning system 2 includes an irrigation source 4 and a suction source 10. The irrigation source 4 and the suction source 10 are in communication with a control module 30 via an irrigation line 6 and a suction line 12, respectively. The control module 30 includes a pump 14 controlling a flow of irrigation fluid between the irrigation source 4 and an endoscope sheath 90. The control module 30 includes a valve 8 controlling suction between the suction source 10 and the endoscope sheath 90 so that suction can be turned off during all or portion of an application cycle of irrigation fluid. The control module 30 includes a power source 20 and a controller and/or microprocessor (not specifically illustrated) in communication with a user interface 31. The user interface 31 controls the control module 30. The irrigation line 6 and the suction line 12 are coupled together with a common fitting 16. The common fitting connects the irrigation line 6 and the suction line 12 to a common line 18/delivery line 42 to supply irrigation fluid, suction, or both to the endoscope sheath 90 for cleaning the endoscope 60.

Any numerical values recited herein include all views from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An endoscope sheath comprising:
   a sheath tube extending along a longitudinal axis between a proximal end and a distal end, the sheath tube is configured to receive a tubular portion of an endoscope;
   a hub connected to the proximal end of the sheath tube; and
   a hub adapter configured to engage the endoscope, wherein the hub adapter includes an arm configured to engage a light post extending from the endoscope so that the hub adapter is restricted from rotating when the sheath tube is rotated about the longitudinal axis,
   wherein the arm on the hub adapter is moveable relative to the sheath between a first locked position and a second locked position, the first and second locked positions laterally opposed to each other such that the light post is capable of extending upward from the hub adapter in the first locked position and is also capable of extending downward from the hub adapter in the second locked position,
   wherein one of the hub adapter and the hub includes a flange, and the other of the hub adapter and the hub includes a channel, the flange comprises a circumferential first series of radial projections, the flange and the first series of radial projections are configured to be received into the channel,
   wherein the flange is configured to rotate within the channel so that the sheath tube is rotatable about the longitudinal axis without rotation of the hub adapter and without the sheath tube and the hub adapter moving axially along the longitudinal axis relative to the endoscope, the channel includes a second series of radial projections cooperating with the first series of radial projections.

2. The endoscope sheath of claim 1, wherein the channel includes a series of mating radial notches, and
   wherein the first series of radial projections are configured to be received into the series of mating radial notches.

3. The endoscope sheath of claim 2, wherein after the flange engages the channel, both a proximal side and a distal side of the flange are constrained within the channel so that the sheath tube is restricted from moving axially along the longitudinal axis relative to the endoscope, and
   wherein after the flange is engaged in the channel, aligning the first series of radial projections with the mating radial notches enables the sheath tube and the hub to separate from the hub adapter and the endoscope.

4. The endoscope sheath of claim 1, wherein hub adapter comprises only a single port for supplying both irrigation fluid and suction to a passageway in the sheath tube that is configured to also receive the tubular portion of the endoscope, and
   wherein the hub adapter includes a through bore so that the tubular portion of the endoscope is capable of passing through the hub adapter when the tubular portion of the endoscope is received in the sheath tube.

5. The endoscope sheath of claim 1, wherein the arm includes a yoke configured to engage the light post so that the hub adapter is prevented from rotating about the longitudinal axis.

6. The endoscope sheath of claim 1, wherein the hub is over molded over the proximal end of the sheath tube.

7. The endoscope sheath of claim 1, wherein the hub is separable from the hub adapter so that the hub and the sheath tube are separable from the hub adapter and the endoscope.

8. The endoscope sheath of claim 1, wherein the hub adapter comprises only a single port, the single port is in communication with both an irrigation source and a suction source, the single port is adapted to provide irrigation fluid from the irrigation source and suction from the suction source to a passageway in the sheath tube that is configured to also receive the tubular portion of the endoscope.

9. The endoscope sheath of claim 1, wherein the distal end of the sheath tube includes an angled tip.

10. The endoscope sheath according to claim 1, wherein a distal end of the hub adapter comprises the flange, and a proximal end of the hub comprises a channel.

11. The endoscope sheath of claim 1, wherein a proximal end of the hub adapter comprises a flare that is configured to abut against a shoulder of the endoscope.

* * * * *